United States Patent
Suzuki et al.

(10) Patent No.: US 12,326,405 B2
(45) Date of Patent: Jun. 10, 2025

(54) EQUOL MEASUREMENT KIT AND EQUOL MEASUREMENT METHOD

(71) Applicant: DAICEL CORPORATION, Osaka (JP)

(72) Inventors: Motofumi Suzuki, Kyoto (JP); Takao Fukuoka, Kyoto (JP); Youji Suzuki, Tokyo (JP); Ryouta Nakamura, Tokyo (JP); Katsuya Maruo, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 168 days.

(21) Appl. No.: 18/025,743

(22) PCT Filed: Sep. 10, 2021

(86) PCT No.: PCT/JP2021/033305
§ 371 (c)(1),
(2) Date: Mar. 10, 2023

(87) PCT Pub. No.: WO2022/054906
PCT Pub. Date: Mar. 17, 2022

(65) Prior Publication Data
US 2023/0349831 A1    Nov. 2, 2023

(30) Foreign Application Priority Data
Sep. 14, 2020 (JP) ................ 2020-153720

(51) Int. Cl.
*G01N 33/483* (2006.01)
*G01N 21/65* (2006.01)

(52) U.S. Cl.
CPC ......... *G01N 21/658* (2013.01); *G01N 33/483* (2013.01)

(58) Field of Classification Search
CPC .......................... G01N 21/658; G01N 33/483
See application file for complete search history.

(56) References Cited

U.S. PATENT DOCUMENTS

2006/0033910 A1    2/2006  Sun et al.

FOREIGN PATENT DOCUMENTS

| CN | 102633763 A | 8/2012 |
| JP | 2007-514169 A | 5/2007 |

(Continued)

OTHER PUBLICATIONS

Karel Decroos, "Administration of Equol-Producing Bacteria Alters the Equol Production Status in the Simulator of the Gastrointestinal Microbial Ecosystem (SHIME)", 2006 (Year: 2006).*

(Continued)

*Primary Examiner* — Maurice C Smith
(74) *Attorney, Agent, or Firm* — Birch, Stewart, Kolasch & Birch, LLP

(57) ABSTRACT

Provided are an equol determination kit that selectively determines equol with high sensitivity by surface-enhanced Raman scattering, and a method for selectively determining equol with high sensitivity by surface-enhanced Raman scattering. The equol determination kit of the present disclosure determines equol by the surface-enhanced Raman scattering spectroscopy. The method for determination of equol of the present disclosure is a method for determination of equol by the surface-enhanced Raman scattering spectroscopy. In the method, equol is preferably determined by analyzing a peak found in at least one wavelength region selected from the group consisting of 1530 to 1630 $cm^{-1}$, 1230 to 1330 $cm^{-1}$, 1140 to 1240 $cm^{-1}$, and 535 to 635 $cm^{-1}$.

14 Claims, 3 Drawing Sheets

(56) References Cited

FOREIGN PATENT DOCUMENTS

| JP | 2011-108888 A | | 6/2011 | |
|---|---|---|---|---|
| KR | 20080072635 A | * | 8/2008 | ................ A61P 5/30 |

OTHER PUBLICATIONS

Ryo Sekine, "Comparative Analysis of Surface-Enhanced Raman Spectroscopy of Daidzein and Formononetin", 2010 (Year: 2010).*
Wan-Sun Kim, "A low-cost, monometallic, surface-enhanced Raman scattering-functionalized paper platform for spot-on bioassays", 2015 (Year: 2015).*
International Preliminary Report on Patentability and Written Opinion of the International Searching Authority for International Application No. PCT/JP2021/033305, dated Mar. 7, 2023, with an English translation.
International Search Report for International Application No. PCT/JP2021/033305, dated Nov. 16, 2021, with an English translation.
Segawa et al. "Rapid Detection of Synthetic Cannabinoids in Herbal Highs Using Surface-Enhanced Raman Scattering Produced by Gold Nanoparticle Co-Aggregation in a Wet System", Analyst, vol. 144, 2019, pp. 6928-6935 (10 pages total).

* cited by examiner

EQUOL MEASUREMENT KIT AND EQUOL MEASUREMENT METHOD

TECHNICAL FIELD

The present disclosure relates to a kit for determination of equol by surface-enhanced Raman scattering spectroscopy, and a method for determination of equol. The present disclosure claims priority to JP 2020-153720 filed in Japan on Sep. 14, 2020, the content of which is incorporated herein.

BACKGROUND ART

Equol is a compound formed by metabolism of daidzein, a type of isoflavone, by equol-producing bacteria. Equol is a compound having a physiological activity similar to female hormones. Equol produced in the body supplements a female hormone level reduced due to menopausal symptoms or the like.

However, depending on an individual, the individual may not have equol-producing bacteria, and in such a case, intake of equol is necessary for supplementing the reduced female hormone level. Therefore, confirmation of whether or not equol is produced in the body is important.

Whether or not equol is produced in the body can be determined by measuring a content of equol in urine or blood. However, since the urine and blood contain a large amount of isoflavones (hereinafter, also referred to as "equol-like substances") such as daidzein having a similar structure to that of equol, in addition to the equol, selective detection and quantification of equol are difficult.

As a method to selectively detect and quantify equol, a separation and analysis method using a large instrument such as HPLC or MS, and a method utilizing specific interactions such as antigen-antibody reactions have been known.

Patent Document 1 describes a method of quantifying equol by bringing a specimen into contact with a labelled substance that immunospecifically binds to equol, i.e., a labelled binding body, and measuring the amount of the labelled binding body that binds to equol or the amount of the labelled binding body that remains without binding to equol using an immunochromatography method. However, the method of Patent Document 1 has problems such as complicated procedure and concerns in accuracy from the perspective of cross-reactivity of the labelled binding body.

CITATION LIST

Patent Document

Patent Document 1: JP 2011-106886 A

SUMMARY OF INVENTION

Technical Problem

An object of the present disclosure is to provide an equol determination kit that selectively determines equol with high sensitivity by surface-enhanced Raman scattering.

Another object of the present disclosure is to provide a method for selective and highly sensitive determination of equol by surface-enhanced Raman scattering.

Yet another object of the present disclosure is to provide a method for testing, using surface-enhanced Raman scattering, whether a subject has equol-producing ability.

Still another object of the present disclosure is to provide a surface-enhanced Raman scattering agent for determination of equol.

Solution to Problem

As a result of diligent research to solve the problems described above, the inventors of the present invention found that, in the surface-enhanced Raman scattering spectroscopy that identifies or quantifies a substance based on a spectrum of amplified Raman scattered light obtained by amplification of Raman scattered light, the characteristic Raman peaks of equol can be identified, and thus equol can be selectively identified and quantified with high sensitivity in a specimen in which equol and equol-like substances are mixed. The present disclosure has been completed based on these findings.

That is, the present disclosure provides an equol determination kit, the kit determining equol by surface-enhanced Raman scattering spectroscopy.

The present disclosure also provides a method for determination of equol, the method determining equol by surface-enhanced Raman scattering spectroscopy.

The present disclosure also provides the method for determination of equol described above, where equol is determined by analyzing a peak found in at least one wavelength region selected from the group consisting of 1530 to 1630 $cm^{-1}$, 1230 to 1330 $cm^{-1}$, 1140 to 1240 $cm^{-1}$, and 535 to 635 $cm^{-1}$.

The present disclosure also provides a method for testing equol-producing ability, the method testing whether a subject has equol-producing ability, the method including determining equol in a specimen collected from the subject by the method for determination of equol described above.

The present disclosure also provides a surface-enhanced Raman scattering agent for determination of equol, the surface-enhanced Raman scattering agent containing a noble metal component.

Advantageous Effects of Invention

With the use of the equol determination kit according to an embodiment of the present disclosure, equol can be detected with high sensitivity. Even for a specimen in which equol and equol-like substances are mixed, equol and the equol-like substances can be distinguished, and the equol concentration in the specimen can be determined with good sensitivity.

Furthermore, in the method for determination of equol of the present disclosure, equol can be determined rapidly with high sensitivity without use of a large-scale separation analysis such as HPLC, and the method is suitable for simple examination of equol using a gel-type sensor or test paper.

DESCRIPTION OF EMBODIMENTS

Equol Determination Kit

Figure 1:
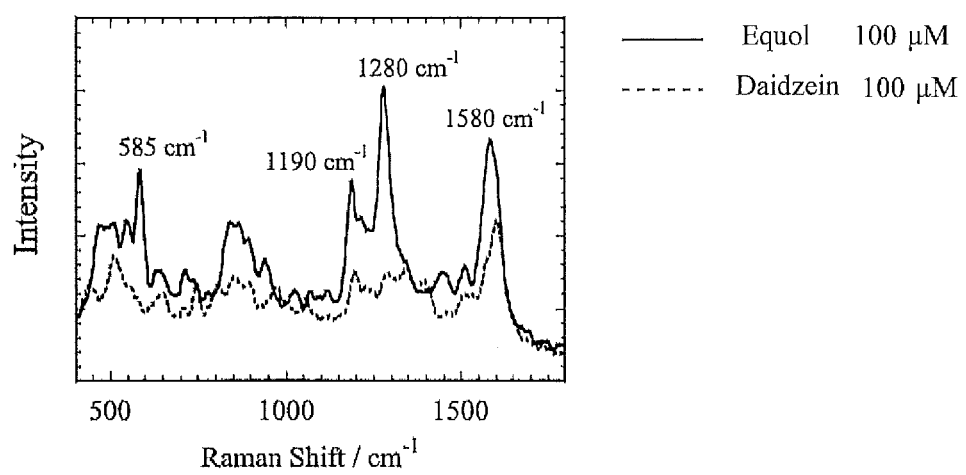
FIG. 1 is a diagram showing Raman shifts of an equol solution having a concentration of 100 μM and a daidzein solution having a concentration of 100 μM.

The equol determination kit according to an embodiment of the present disclosure is a kit for determination of equol by the surface-enhanced Raman scattering spectroscopy. More specifically, the equol determination kit is a kit for quantification and/or identification of equol based on the characteristic Raman peak of equol.

The kit includes at least a device capable of identifying at least one characteristic Raman peak of equol. As the device, a Raman spectrometer (e.g., including a light source, a filter for removing Rayleigh scattered light, a spectroscope for separating Raman scattered light into a spectrum, and a detector) is preferred.

As the light source, for example, a light source emitting a laser beam (preferably a near infrared laser beam) is preferred.

The kit preferably further includes a surface-enhanced Raman scattering agent. Note that the surface-enhanced Raman scattering agent will be described below.

With the use of the kit, selective quantification of a trace amount of equol can be performed by the same method as the method for determination of equol described below.

In general, the limit of the equol concentration that can be measured by Raman spectroscopy is at most approximately 10 mmol/L. However, with the use of the equol determination kit according to an embodiment of the present disclosure, equol can be quantified with high accuracy even when the equol content in a specimen is extremely small. The quantification limit concentration in a case where equol is determined by using the equol determination kit according to an embodiment of the present disclosure is, for example, 1 μmol/L.

Furthermore, with the use of the kit, whether a subject has equol-producing ability or not can be determined by testing a specimen of the subject. Therefore, the kit may be an equol-producing ability test kit.

Method for Determination of Equol

The method for determination of equol according to an embodiment of the present disclosure is a method for determination of equol by the surface-enhanced Raman scattering spectroscopy.

In the method for determination of equol, equol in a specimen, in which equol and equol-like substances are mixed, can be selectively determined (quantified and/or identified) by analyzing a peak that appears characteristically for equol, i.e., a peak that appears for equol but does not appear for equol-like substances.

The peak that characteristically appears for equol varies slightly depending on experimental conditions such as a used measurement instrument; however, examples thereof include a peak (=peak having a peak position in the wavelength region) found in at least one wavelength region selected from the group consisting of 1530 to 1630 $cm^{-1}$, 1230 to 1330 $cm^{-1}$, 1140 to 1240 $cm^{-1}$, and 535 to 635 $cm^{-1}$, and preferably a peak found in at least one wavelength region selected from the group consisting of 1570 to 1590 $cm^{-1}$, 1270 to 1290 $cm^{-1}$, 1180 to 1200 $cm^{-1}$, and 570 to 590 $cm^{-1}$.

In the determination method, as a means for enhancing Raman scattered light of equol, a surface-enhanced Raman scattering agent is preferably used. Note that the surface-enhanced Raman scattering agent will be described below.

The method for determination of equol according to an embodiment of the present disclosure includes the following procedure, for example.

1. The surface-enhanced Raman scattering agent is brought into contact with a specimen, and a test specimen is thus formed.
2. The test specimen is irradiated with irradiation light from a light source to produce scattered light (including Raman scattered light and Rayleigh scattered light)
3. The scattered light is passed through a filter to remove the Rayleigh scattered light.
4. The scattered light after the Rayleigh scattered light has been removed is introduced to a spectroscope, and the introduced scattered light is separated into a spectrum by the spectroscope.
5. The spectrum is detected with a detector.

The method of bringing the surface-enhanced Raman scattering agent into contact with a specimen is not particularly limited as long as the method is a method that can bring the surface-enhanced Raman scattering agent (preferably a surface of a noble metal component in the surface-enhanced Raman scattering agent) into contact with the specimen. Examples thereof include a method in which the surface-enhanced Raman scattering agent is immobilized onto a surface of a substrate and then adding a liquid specimen (in a case where the specimen is not liquid, a specimen formed into a liquid form) dropwise thereto, and a method in which the surface-enhanced Raman scattering agent and a liquid specimen are mixed on a sample stage or the like.

According to the method for determination of equol, since the Raman scattering of equol contained in the specimen is amplified by using the surface-enhanced Raman scattering agent, selective quantification of equol with high sensitivity can be performed.

Surface-Enhanced Raman Scattering Agent

The surface-enhanced Raman scattering agent is a surface-enhanced Raman scattering agent used for determination of equol by the surface-enhanced Raman scattering spectroscopy. Thus, the surface-enhanced Raman scattering agent may be a surface-enhanced Raman scattering agent for determination of equol.

The surface-enhanced Raman scattering agent preferably contains a noble metal component. The surface-enhanced Raman scattering agent may contain one or more types selected from, for example, solvents, thickeners, surfactants, and dispersion stabilizers (e.g., citric acid), in addition to the noble metal component.

In the surface-enhanced Raman scattering agent, the noble metal component may be immobilized to a substrate, or the noble metal component may be dispersed in a dispersion medium. In particular, from the perspectives of increasing enhancement effect of the Raman scattered light and improving identification accuracy, the noble metal component is preferably dispersed in a dispersion medium, particularly preferably dispersed in a viscous dispersion medium, and especially preferably dispersed in a gelatinous dispersion medium. Thus, the surface-enhanced Raman scattering agent is preferably a noble metal dispersion, and especially preferably a gelatinous noble metal dispersion.

The viscosity of the dispersion medium (preferably a viscous dispersion medium, and particularly preferably a gelatinous dispersion medium) at 25° C. and a shear rate of 10 (1/s) is preferably, for example, 50 mPa·s or greater from the perspective of increasing enhancement effect of the Raman scattered light.

Furthermore, in the noble metal dispersion, the noble metal component may be dispersed in a colloidal state. That is, the noble metal dispersion may be a noble metal colloidal solution.

The viscosity of the noble metal dispersion (in particular, a gelatinous noble metal dispersion) at 25° C. and a shear rate of 10 (1/s) is, for example, from 50 to 100000 mPa·s, preferably from 100 to 50000 mPa·s, and particularly preferably from 200 to 30000 mPa·s.

Note that the viscosities of the dispersion and the dispersion medium can be measured by using a viscosity-viscoelasticity measuring instrument (rheometer) (trade name "RheoStress 600", available from HAAKE).

According to the surface-enhanced Raman scattering agent, even if a content of equol in a specimen (e.g., urine, blood, or intestinal contents of a subject, or a supernatant of these) is extremely small, the equol content can be measured with high accuracy.

When an adult subject has equol-producing ability, the equol concentration in urine is typically from 1 to 75 µmol/L. Thus, when equol contained in urine of a subject is measured by using the surface-enhanced Raman scattering agent, determination of whether the subject has equol-producing ability (or whether the subject has equol-producing bacteria) can be easily performed.

Noble Metal Component

As the noble metal component, at least one noble metal component selected from the group consisting of gold, silver, and copper is preferred.

Solvent

The solvent is a component constituting the dispersion medium. As the solvent, use of a solvent that can highly disperse the noble metal component and that has a low Raman activity is preferred from the perspective of enhancing quantitative accuracy of equol.

The solvent includes water-based solvents and oil-based solvents. Specific examples of the solvent include water, alcohols, and oils. One of these can be used alone or two or more in combination.

Examples of the alcohol include alcohols such as methanol, ethanol, propanol, and butanol; and polyhydric alcohols such as ethylene glycol, propylene glycol, butylene glycol, and glycerin.

Examples of the oil include hydrocarbon oils such as mineral oil and liquid paraffin; animal and vegetable oils such as sunflower oil, macadamia nut oil, avocado oil, almond oil, wheat germ oil, rice germ oil, olive oil, soybean oil, corn oil, castor oil, beef tallow, jojoba oil, evening primrose oil, coconut oil, camellia oil, rosehip oil, squalane, turtle oil, mink oil, egg yolk oil, lanolin, spermaceti, candelilla wax, montan wax, rice wax, lanolin wax, and shellac; hydrocarbon oils such as hexane, cyclohexane, isododecane, benzene, toluene, poly-α-olefin, and liquid paraffin; ethers such as tetrahydrofuran; halogenated hydrocarbons such as carbon tetrachloride and chlorobenzene; petroleum components such as kerosene, gasoline, diesel, and heavy oil; silicone oils such as dimethylpolysiloxane and methylphenylpolysiloxane; ester oils such as octyldodecyl oleate, cetyl eythylhexanoate, glyceryl triisooctanoate, and neopentyl glycol diisooctanoate; higher alcohols such as hexadecyl alcohol and oleyl alcohol; higher fatty acids such as lauric acid, isostearic acid, and oleic acid; aromatic carboxylic acids, and pyridine.

Examples of the solvent having a high Raman activity include N,N-dimethylformamide (DMF), dimethyl sulfoxide (DMSO), dimethylacetamide (DMAA), N-methylpyrrolidone (NMP), tetrahydrofuran (THF), cyclohexanone, lactam, lactone, and N,N,N,N-tetramethylurea. When these solvents are used, the used amount thereof (in a case where two or more types are combined for use, the total amount thereof) is, for example, preferably 30 wt. % or less, more preferably 20 wt. % or less, particularly preferably 10 wt. % or less, most preferably 5 wt. % or less, and especially preferably 1 wt. % or less, with respect to the total amount of the solvent contained in the surface-enhanced Raman scattering agent.

Thickener

In a case where the solvent has a low viscosity, a thickener may be added for thickening. The thickener can be appropriately selected based on the type of the solvent.

In a case where a water-soluble solvent is used as the solvent, examples of the thickener include cellulose-based polymer compounds such as hydroxyethyl cellulose, methyl cellulose, ethyl cellulose, and carboxymethyl cellulose; plant-based natural polymer compounds such as carrageenan and guar gum; microorganism-based natural polymer compounds such as xanthan gum; animal-based natural polymer compounds such as casein and gelatin; starch-based polymer compounds such as carboxymethyl starch; vinyl-based polymer compounds such as polyvinyl alcohol, polyvinylpyrrolidone, sodium polyacrylate, and carboxyvinyl polymers; polyether-based polymer compounds such as polyethylene glycol, polypropylene glycol, and polyglycerin; and polyoxyalkylene-modified saccharides such as polyoxyethylene methyl glucoside and polyoxypropylene methyl glucoside.

In a case where an oil-based solvent is used as the solvent, examples of the thickener include sugar fatty acid esters, 12-hydroxystearic acid, 1,3;2,4-dibenzylidene-D-sorbitol, N-lauroyl-L-glutamic acid-α,γ-bis-n-butylamide, benzene fatty acid amides, and cyclohexane fatty acid amides. Furthermore, examples of the sugar fatty acid esters include dextrin fatty acid esters such as dextrin palmitate and dextrin myristate; and inulin fatty acid esters such as inulin stearate.

Method for Testing Equol-Producing Ability

The method for testing equol-producing ability is a method to test whether a subject has an ability to produce equol. Furthermore, the method for testing equol-producing ability includes determining equol in a specimen collected from a subject by the method for determination of equol described above.

In a case where a subject has equol-producing ability, the subject has equol-producing bacteria in the intestine. When the subject ingests daidzein, which is a type of isoflavone, equol is produced by metabolism of daidzein by equol-producing bacteria. The produced equol is absorbed by the intestinal tract and taken into the blood, and part of the equol is excreted into the urine. Thus, as such, by determining equol contained in a specimen that is urine, blood, intestinal contents, or a supernatant obtained by subjecting urine, blood, or intestinal contents to centrifugation, whether a subject has equol-producing ability or whether a subject has equol-producing bacteria can be easily determined.

Examples of the equol-producing bacteria include microorganisms of the genus *Lactococcus*, the genus *Slackia*, the genus *Adlercreutzia*, the genus *Asaccharobacter*, and the genus *Eggerthella*. More specific examples thereof include

*Lactococcus garvieae, Adlercreulzia equolifaciens, Asaccharobacter celatus*, and *Eggerthella* sp. YY7918.

For example, when an adult subject has equol-producing ability, the equol concentration in urine is typically from 1 to 75 μmol/L. Thus, if the equol concentration is not less than the range described above in the determination of equol contained in urine of a subject, it can be determined that the subject has equol-producing ability. If the equol concentration is below the range described above, it can be determined that the subject does not have equol-producing ability.

In the method for testing equol-producing ability, since equol is selectively determined with high sensitivity by the method for determination of equol described above, presence/absence of equol-producing ability or equol producing bacteria can be determined with high accuracy.

Each of the configurations, their combinations, and the like of the present disclosure above is an example, and addition, omission, substitution, and change of the configuration can be appropriately made without departing from the gist of the present disclosure. In addition, the present disclosure is not limited by the embodiments and is limited only by the claims.

EXAMPLES

Hereinafter, the present disclosure will be described more specifically with reference to examples, but the present disclosure is not limited by these examples.

Preparation Example 1 (Sample Preparation)

A 10 mM equol solution in ethanol was diluted with water and ethanol, and thus an equol solution having a concentration of 1 μM and an equol solution having a concentration of 100 μM were prepared.

Preparation Example 2 (Sample Preparation)

An approximately 420 μM daidzein solution was diluted with water and ethanol, and thus a daidzein solution having a concentration of 100 μM was prepared.

Example 1

Equol was determined in accordance with a method described in H. Segawa, T. Fukuoka, T. Itoh, Y. Imai, Y. T. Iwata, T. Yamamuro, K. Kuwayama, K. Tsujikawa, T. Kanamori, and H. Inoue, Analyst, 144, 6928-6935 (2019).

That is, in a container, 3 μL of the 100 μM equol solution obtained in Preparation Example 1, 3 μL of 1 M sodium chloride solution, and 54 μL of colloidal gold solution were added and mixed.

In a measurement chamber of a Raman spectrometer 1 (trade name "RAM mini" available from Lambda Vision Inc.), the container was set and irradiation of laser beam (wavelength of laser beam: 785 nm) for 1 second was repeated 4 times to generate Raman scattered light, and the average thereof was recorded. The time required for the mixing and the measurement was less than 30 seconds. Furthermore, the same procedure was performed for the solvent used for sample preparation and used as a background.

Note that, for the measurement of the surface-enhanced Raman scattering, the co-aggregation method was used, which is a wet analysis method suitable for initial screening.

Comparative Example 1

The same procedure as in Example 1 was performed except for using the 100 μM daidzein solution obtained in Preparation Example 2 in place of the 100 μM equol solution.

The results of Example 1 and Comparative Example 1 are shown in FIG. 1. As can be seen from FIG. 1, for the 100 μM equol solution, characteristic peaks were found around 1580 $cm^{-1}$, 1280 $cm^{-1}$, 1190 $cm^{-1}$, and 590 $cm^{-1}$. On the other hand, for the 100 μM daidzein solution, peaks were not found around the above wavelength regions.

Example 2

The same procedure as in Example 1 was performed except for using the 1 μM equol solution in place of the 100 μM equol solution.

Figure 2:
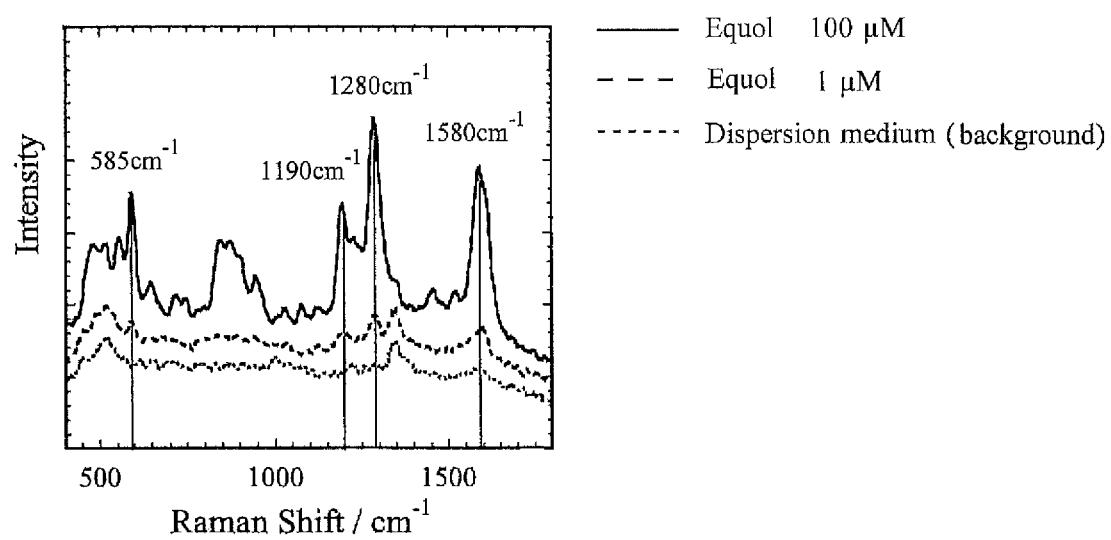
FIG. 2 is a diagram showing Raman shifts of equol solutions having a concentration of 1 μM and a concentration of 100 μM and a Raman shift of a solvent used in the solutions (as a background).

The results of Example 1 and Example 2 are shown in FIG. 2. As can be seen from FIG. 2, even for the equol concentration of 1 μM, characteristic peaks of equol, which were found around 1580 $cm^{-1}$, 1280 $cm^{-1}$, 1190 $cm^{-1}$, and 590 $cm^{-1}$, were observed similarly to the case of the equol concentration of 100 μM. As such, it was confirmed that the method according to an embodiment of the present disclosure can selectively quantify a trace amount of equol.

Example 3

A substrate containing gold nanorods as a noble metal component (wavelet substrate, available from Nidek Co., Ltd.) was used as the surface-enhanced Raman scattering substrate.

Figure 3:
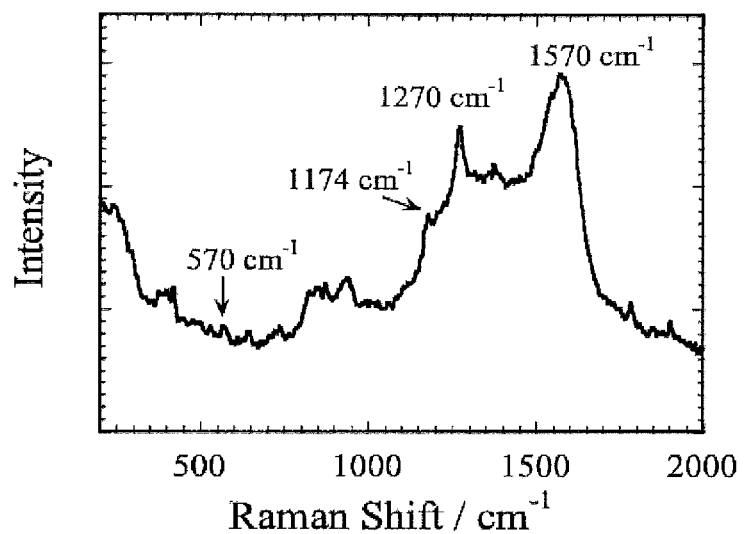
FIG. 3 is a surface-enhanced Raman scattering spectrum obtained from the measurement in which 1 μL of an equol solution having a concentration of 100 μM is added dropwise on a surface-enhanced Raman scattering substrate.

1 μL of the equol solution having a concentration of 100 μM obtained in Preparation Example 1 was added dropwise onto the surface-enhanced Raman scattering substrate and naturally dried. The substrate was set to a measurement site of a Raman spectrometer 2 (trade name "RAM 200" available from Lambda Vision Inc.) equipped with a laser of 785 nm, and laser irradiation for 1 second was repeated 4 times, and the average thereof was recorded. Characteristic peaks were observed around 1570 $cm^{-1}$, 1270 $cm^{-1}$, 1174 $cm^{-1}$, and 570 $cm^{-1}$ (FIG. 3).

Note that the Raman spectrum of diamond as a reference material was measured by the Raman spectrometer 2. The result showed that a sharp peak was observed at 1322 $cm^{-1}$. It is known that a Raman peak appears around 1332 $cm^{-1}$ for single crystal diamond, and thus it was confirmed that the peak positions measured by the Raman spectrometer 2 was shifted toward lower wavelength by approximately 10 $cm^{-1}$.

Taking the above into consideration, the peak positions can be corrected to approximately 1580 $cm^{-1}$, 1280 $cm^{-1}$, 1184 $cm^{-1}$, and 580 $cm^{-1}$.

It was found that, when a different type of spectrometer was used, peak positions were shifted; however, if the shifts of the peak positions were corrected based on the shift of the peak position of the reference material, at least one peak position matched. It was found that equol can be determined based on the Raman peaks when the peaks for which peak positions were matched were utilized.

As a summary of the above, configurations and variations of the present disclosure are described below.

[1] An equol determination kit, the kit determining equol by surface-enhanced Raman scattering spectroscopy.

[2] The equol determination kit according to [1] including a Raman spectrometer.

[3] The equol determination kit according to [1] or [2] including a surface-enhanced Raman scattering agent.

[4] The (equol determination kit according to [1] or [2] including a surface-enhanced Raman scattering agent containing a noble metal component.

[5] The equol determination kit according to [1] or [2] including a surface-enhanced Raman scattering agent containing at least one noble metal component selected from the group consisting of gold, silver, and copper.

[6] The equol determination kit according to [1] or [2] including a surface-enhanced Raman scattering agent containing a noble metal component dispersed in a viscous dispersion medium.

[7] including a surface-enhanced Raman scattering agent containing a noble metal component dispersed in a gelatinous dispersion medium.

[8] The equol determination kit according to [1] or [2] including a gelatinous noble metal dispersion.

[9] The equol determination kit according to [1] or [2] including a gelatinous noble metal dispersion having a viscosity of 50 mPa·s or greater at 25° C. and a shear rate of 10 (1/s).

[10] The equol determination kit according to [1] or [2] including a noble metal colloidal solution.

[11] the equol determination kit according to [1] or [2] including a substrate immobilized with a noble metal component.

[12] A method for determination of equol, the method determining equol by surface-enhanced Raman scattering spectroscopy.

[13] The method for determination of equol according to [12], where equol is determined by analyzing a peak found in at least one wavelength region selected from the group consisting of 1530 to 1630 $cm^{-1}$, 1230 to 1330 $cm^{-1}$, 1140 to 1240 $cm^{-1}$, and 535 to 635 $cm^{-1}$.

[14] The method for determination of equol according to [12], where equol is determined by analyzing a peak found in at least one wavelength region selected from the group consisting of 1570 to 1590 $cm^{-1}$, 1270 to 1290 $cm^{-1}$, 1180 to 1200 $cm^{-1}$, and 570 to 590 $cm^{-1}$.

[15] A method for testing equol-producing ability, the method testing whether a subject has equol-producing ability, the method including determining equol in a specimen collected from a subject by the method for determination of equol according to any one of [12] to [14].

[16] A surface-enhanced Raman scattering agent for determination of equol, the surface-enhanced Raman scattering agent containing a noble metal component.

[17] The surface-enhanced Raman scattering agent for determination of equol according to [16] containing a surface-enhanced Raman scattering agent containing at least one noble metal component selected from the group consisting of gold, silver, and copper.

[18] The surface-enhanced Raman scattering agent for determination of equol according to [16] containing the noble metal component and a viscous dispersion medium.

[19] The surface-enhanced Raman scattering agent for determination of equol according to [16] containing the noble metal component and a gelatinous dispersion medium.

[20] The surface-enhanced Raman scattering agent for determination of equol according to [16] containing a gelatinous noble metal dispersion.

[21] The surface-enhanced Raman scattering agent for determination of equol according to [16] containing a gelatinous noble metal dispersion having a viscosity of 50 mPa·s or greater at 25° C. and a shear rate of 10 (1/s).

[22] The surface-enhanced Raman scattering agent for determination of equol according to [16] containing a noble metal colloidal solution.

INDUSTRIAL APPLICABILITY

With the use of the equol determination kit according to an embodiment of the present disclosure, equol can be rapidly detected with high sensitivity. Even for a specimen in which equol and equol-like substances are mixed, equol and the equol-like substances can be distinguished, and the equol concentration in the specimen can be determined with good sensitivity.

The invention claimed is:

1. An equol determination kit, the kit determining equol by surface-enhanced Raman scattering spectroscopy, wherein the equol determination kit comprises a surface-enhanced Raman scattering agent which is a noble metal dispersion having a viscosity of 50 mPa·s or greater at 25° C. and a shear rate of 10 (1/s).

2. A method for determination of equol, the method determining equol by surface-enhanced Raman scattering spectroscopy, comprising bringing a surface-enhanced Raman scattering agent into contact with a specimen, wherein the surface-enhanced Raman scattering agent is a noble metal dispersion having a viscosity of 50 mPa·s or greater at 25° C. and a shear rate of 10 (1/s).

3. The method for determination of equol according to claim 2, wherein equol is determined by analyzing a peak found in at least one wavelength region selected from the group consisting of 1530 to 1630 $cm^{-1}$, 1230 to 1330 $cm^{-1}$, 1140 to 1240 $cm^{-1}$, and 535 to 635 $cm^{-1}$.

4. A method for testing equol-producing ability, the method testing whether a subject has equol-producing ability, the method comprising determining equol in a specimen collected from a subject by the method for determination of equol according to claim 2.

5. A surface-enhanced Raman scattering agent for determination of equol, the surface-enhanced Raman scattering agent comprising a noble metal component, further comprising a dispersion medium having a viscosity of 50 mPa·s or greater at 25° C. and a shear rate of 10 (1/s).

6. The equol determination kit according to claim 1, comprising a surface-enhanced Raman scattering agent containing at least one noble metal component selected from the group consisting of gold, silver, and copper.

7. The equol determination kit according to claim 1, comprising a surface-enhanced Raman scattering agent containing at least one noble metal component selected from the group consisting of gold, silver, and copper dispersed in a viscous dispersion medium.

8. The equol determination kit according to claim 1, wherein the surface-enhanced Raman scattering agent contains at least one noble metal component selected from the group consisting of gold, silver, and copper dispersed in a dispersion medium and is a gelatinous noble metal dispersion having a viscosity of from 50 to 100000 mPa·s at 25° C. and a shear rate of 10 (1/s).

9. The equol determination kit according to claim 1, wherein the equol determination kit is an equol-producing ability test kit for testing whether a subject has equol-producing ability.

10. The method for determination of equol according to claim 2, wherein the method includes bringing a surface-enhanced Raman scattering agent into contact with a specimen, and the specimen is urine, blood, or intestinal contents of a subject, or a supernatant obtained by subjecting urine, blood, or intestinal contents of a subject to centrifugation.

11. The method for determination of equol according to claim 2, wherein the method includes bringing a surface-enhanced Raman scattering agent into contact with a specimen, and the surface-enhanced Raman scattering agent is a noble metal dispersion containing at least one noble metal component selected from the group consisting of gold, silver, and copper dispersed in a viscous dispersion medium.

12. The method for determination of equol according to claim 2, wherein the method includes bringing a surface-enhanced Raman scattering agent into contact with a specimen, and the surface-enhanced Raman scattering agent is a noble metal colloidal solution.

13. The method for determination of equol according to claim 2, wherein the method includes bringing a surface-enhanced Raman scattering agent into contact with a specimen, and the surface-enhanced Raman scattering agent is a gelatinous noble metal dispersion having a viscosity of from 50 to 100000 mPa·s at 25° C. and a shear rate of 10 (1/s).

14. A method for testing equol-producing ability, the method testing whether a subject has equol-producing ability, the method including: bringing a surface-enhanced Raman scattering agent into contact with a specimen, the specimen being urine, blood, or intestinal contents of a subject, or a supernatant obtained by subjecting urine, blood, or intestinal contents of a subject to centrifugation; and determining equol by surface-enhanced Raman scattering spectroscopy, wherein the surface-enhanced Raman scattering agent is a noble metal dispersion having a viscosity of 50 mPa·s or greater at 25° C. and a shear rate of 10 (1/s).

* * * * *